(12) United States Patent
Lee et al.

(10) Patent No.: US 10,945,940 B2
(45) Date of Patent: Mar. 16, 2021

(54) METHOD OF PREPARING ULTRA-LOW MOLECULAR WEIGHT KERATIN PEPTIDE

(71) Applicant: KYUNGPOOK NATIONAL UNIVERSITY INDUSTRY-ACADEMIC COOPERATION FOUNDATION, Buk-gu Daegu (KR)

(72) Inventors: Dong Woo Lee, Buk-gu Daegu (KR); Nam Joo Kang, Buk-gu Daegu (KR); Yong Jik Lee, Suseong-gu Daegu (KR); Hyeon Su Jin, Dong-gu Daegu (KR); In Hyuk Yeo, Buk-gu Daegu (KR); Kyeong Seop Song, Gyeongsangbuk-do (KR); Jae-Eun Lee, Buk-gu Daegu (KR)

(73) Assignee: KYUNGPOOK NATIONAL UNIVERSITY INDUSTRY-ACADEMIC COOPERATION FOUNDATION, Buk-Gu Daegu (KR)

( * ) Notice: Subject to any disclaimer, the term of this patent is extended or adjusted under 35 U.S.C. 154(b) by 147 days.

(21) Appl. No.: 15/771,747

(22) PCT Filed: Oct. 31, 2016

(86) PCT No.: PCT/KR2016/012410
§ 371 (c)(1),
(2) Date: Apr. 27, 2018

(87) PCT Pub. No.: WO2017/074163
PCT Pub. Date: May 4, 2017

(65) Prior Publication Data
US 2018/0344608 A1 Dec. 6, 2018

(30) Foreign Application Priority Data

Oct. 29, 2015 (KR) .................. 10-2015-0150618
Oct. 31, 2016 (KR) .................. 10-2016-0143527

(51) Int. Cl.
| | | |
|---|---|---|
| *A61K 8/65* | (2006.01) | |
| *A23L 33/18* | (2016.01) | |
| *B01D 15/34* | (2006.01) | |
| *B01D 15/36* | (2006.01) | |
| *C07K 1/18* | (2006.01) | |
| *C07K 1/16* | (2006.01) | |
| *C07K 1/34* | (2006.01) | |
| *C07K 1/36* | (2006.01) | |
| *A61Q 19/08* | (2006.01) | |
| *C07K 14/47* | (2006.01) | |

(Continued)

(52) U.S. Cl.
CPC ................ *A61K 8/65* (2013.01); *A23L 33/18* (2016.08); *A61Q 19/08* (2013.01); *B01D 15/34* (2013.01); *B01D 15/361* (2013.01); *C07K 1/16* (2013.01); *C07K 1/18* (2013.01); *C07K 1/34* (2013.01); *C07K 1/36* (2013.01); *C07K 14/4741* (2013.01); *C12P 21/06* (2013.01); *A23V 2002/00* (2013.01); *B01D 61/145* (2013.01)

(58) Field of Classification Search
CPC combination set(s) only.
See application file for complete search history.

(56) References Cited

U.S. PATENT DOCUMENTS

| | | | |
|---|---|---|---|
| 2007/0207111 A1 | 9/2007 | Nomura et al. | |
| 2010/0196302 A1* | 8/2010 | Vermelho | C12P 21/06 514/1.1 |

FOREIGN PATENT DOCUMENTS

| | | |
|---|---|---|
| JP | 0665044 A | 3/1994 |
| WO | 2000/056144 A1 | 9/2000 |

(Continued)

OTHER PUBLICATIONS

Villa, Ana Lúcia Vazquez et al., Feather Keratin Hydrolysates Obtained From Microbial Keratinases: Effect on Hair Fiber, BMC Biotechnology (Springer Nature), vol. 13, No. 1, 2013, p. 15.*

(Continued)

*Primary Examiner* — Heidi Reese
(74) *Attorney, Agent, or Firm* — Barnes & Thornburg LLP

(57) ABSTRACT

The present disclosure relates to methods of preparing an ultra-low molecular weight keratin peptide and use thereof. In particular, the present disclosure relates to a method of preparing an ultra-low molecular weight keratin peptide using culturing a microorganism having keratinolytic activity in a medium including keratin, ultrafiltration, ion exchange chromatography and gel filtration chromatography, a peptide prepared by the method, and a cosmetic and food composition for preventing or improving skin aging or skin wrinkles including the same. According to the method of preparing a keratin peptide of the present invention, it is possible to eco-friendly biologically treat waste resources and efficiently purify and recover anti-aging functional ultra-low molecular weight keratin peptides. In addition, the keratin peptide of the present disclosure breaks down collagen to have abilities to inhibit MMP-1 expression and activity, which is an enzyme that causes skin aging, which has an excellent effect on anti-skin aging and skin wrinkle improvement and has no toxicity to skin cells. It is suitable for use as a cosmetic, pharmaceutical or food composition for preventing, improving or treating skin aging or skin wrinkles, thereby being effectively used for the efficient and rapid production and development of high value-added functional cosmetic substances.

15 Claims, 7 Drawing Sheets

Specification includes a Sequence Listing.

(51) Int. Cl.
*C12P 21/06* (2006.01)
*B01D 61/14* (2006.01)

(56) References Cited

FOREIGN PATENT DOCUMENTS

| | | |
|---|---|---|
| WO | 2003/064449 A2 | 8/2003 |
| WO | 2009/000057 A2 | 12/2008 |
| WO | 2014/140176 A1 | 9/2014 |

OTHER PUBLICATIONS

PCT International Search Report and Written Opinion for PCT International Application No. PCT/KR2016/012410, completed on Feb. 21, 2017.

* cited by examiner

[FIGURES]
[FIG. 1]
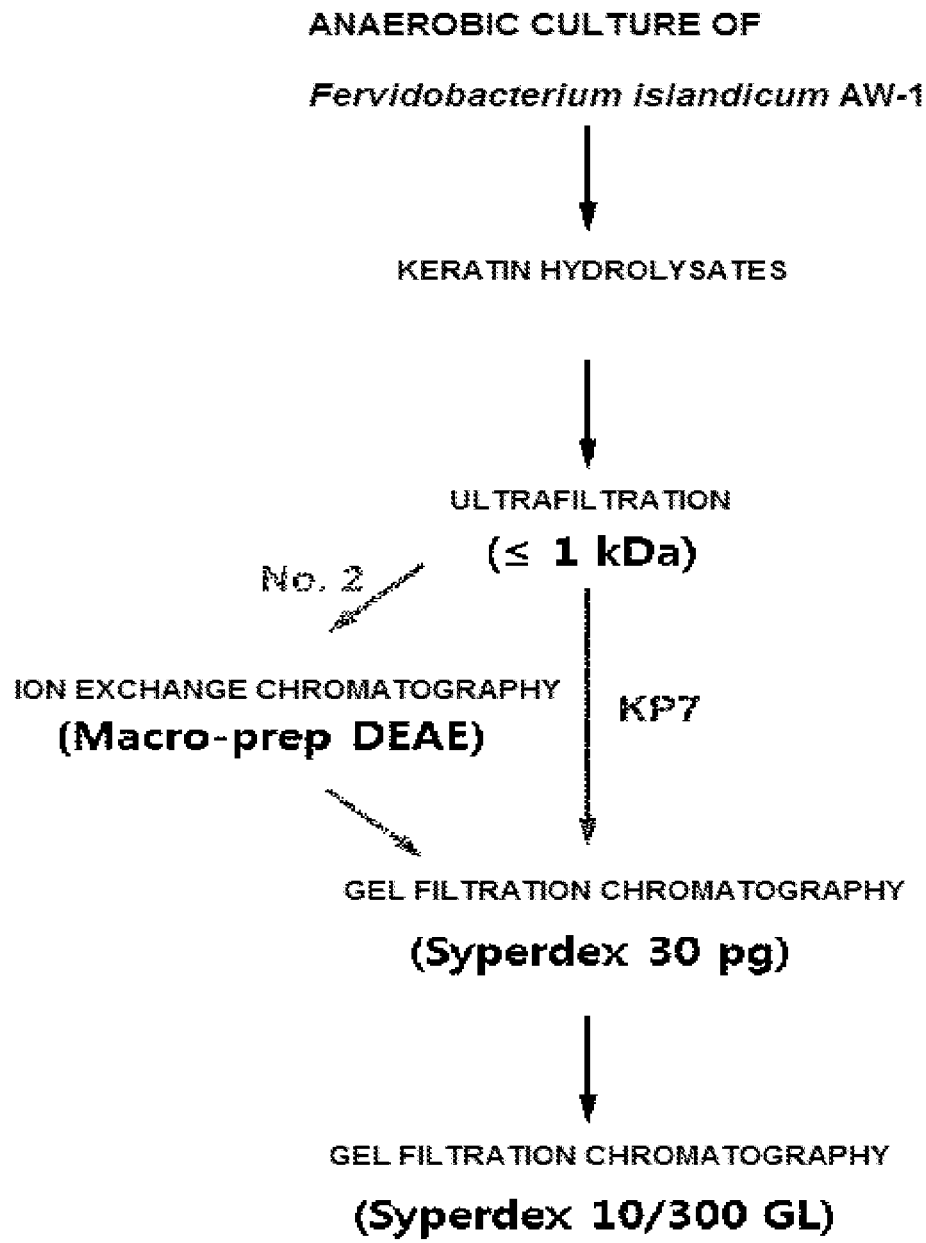

[FIG. 2]
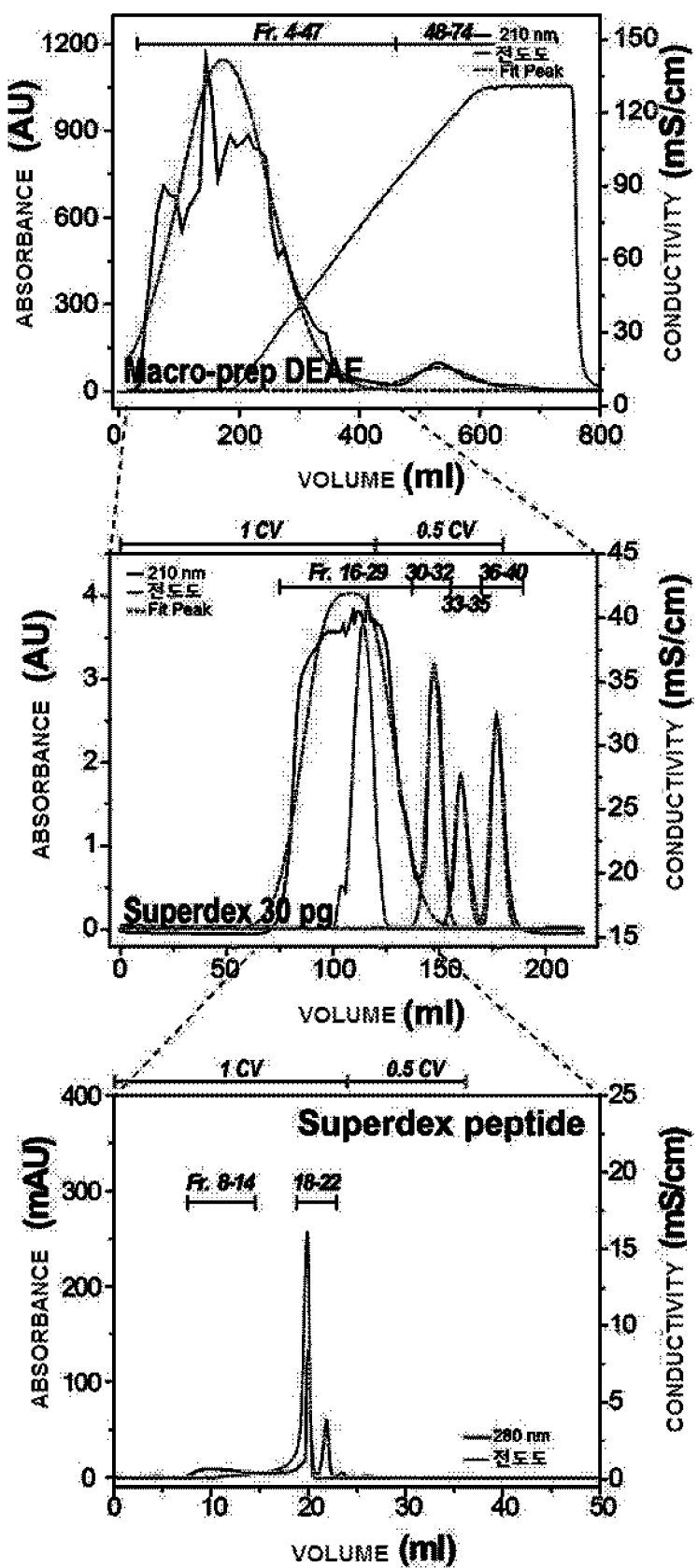

[FIG. 3]
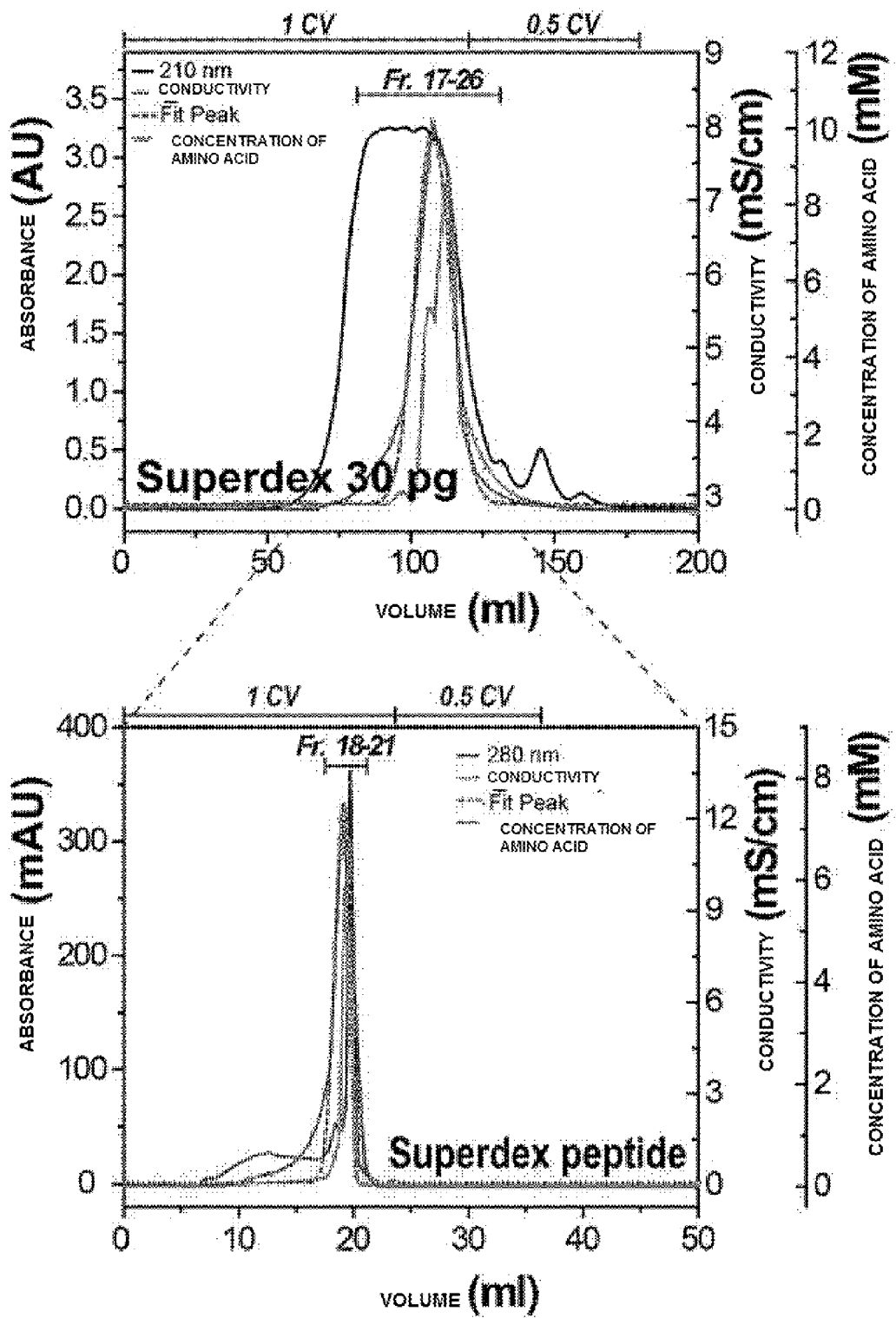

[FIG. 4A]
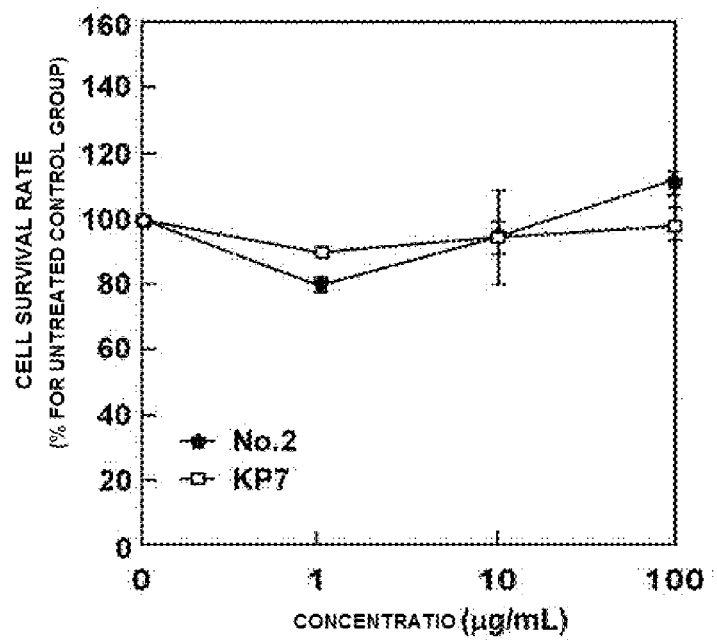
[FIG. 4B]
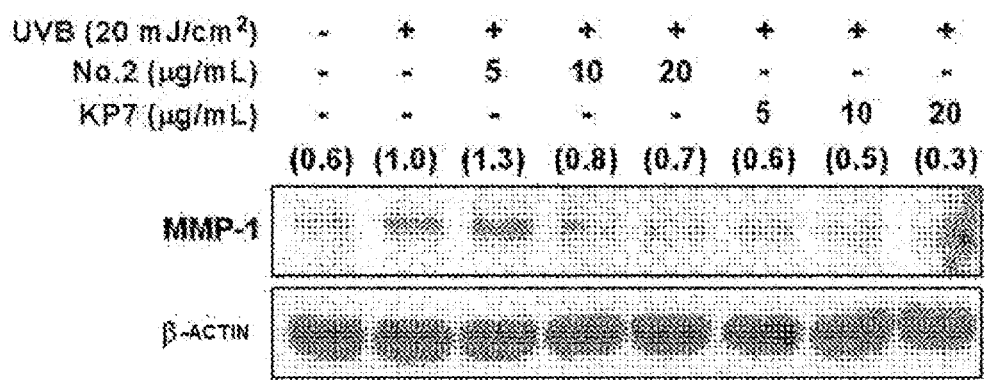

[FIG. 5A]
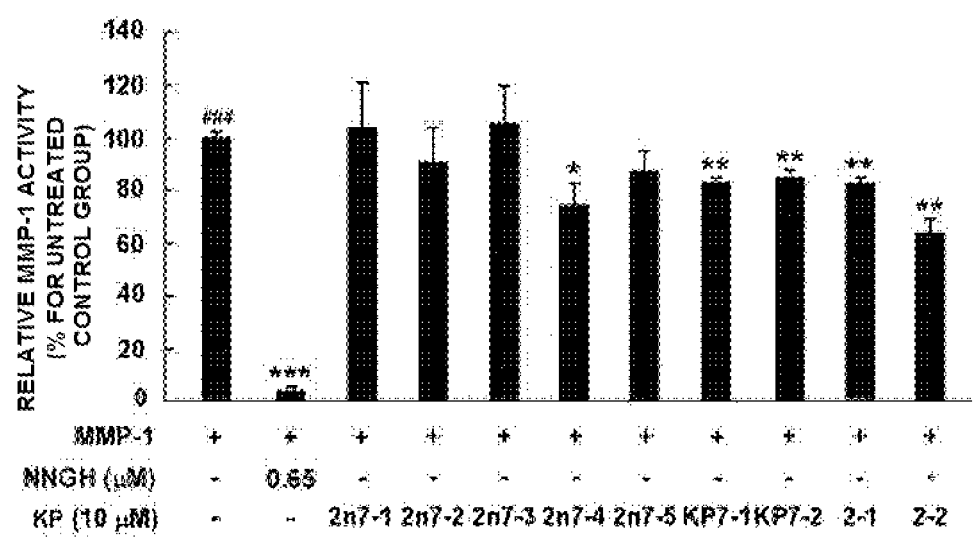

[FIG. 5B]
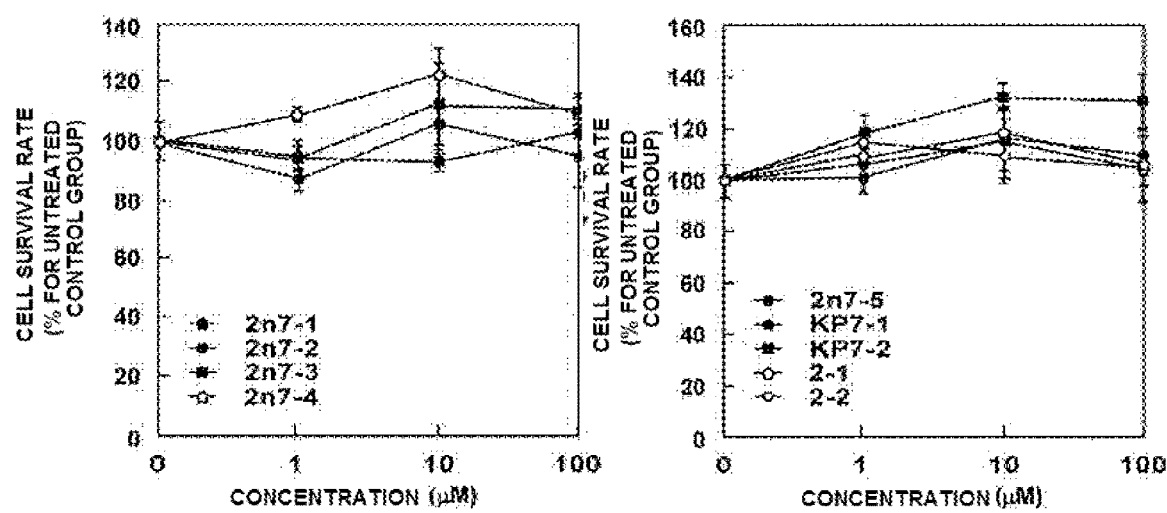

[FIG. 5C]
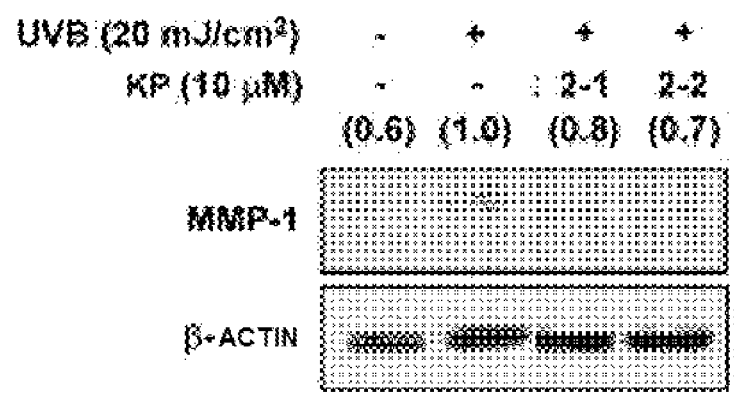

METHOD OF PREPARING ULTRA-LOW MOLECULAR WEIGHT KERATIN PEPTIDE

CROSS-REFERENCE TO RELATED APPLICATIONS

This application is a national stage entry made under 35 U.S.C. § 371(b) of PCT International Application No. PCT/KR2016/012410, filed Oct. 31, 2016, which is based on and claims priority from Korean Patent Application No. 10-2016-0143527, filed Oct. 31, 2016 and Korean Patent Application No. 10-2015-0150618, filed Oct. 29, 2015, with the Korean Intellectual Property Office, the disclosures of which are all incorporated by reference herein in their entirety.

TECHNICAL FIELD

The present disclosure relates to methods of preparing an ultra-low molecular weight keratin peptide and use thereof. In particular, the present disclosure relates to a method of preparing an ultra-low molecular weight keratin peptide using culturing a microorganism having keratinolytic activity in a medium including keratin, ultrafiltration, ion exchange chromatography and gel filtration chromatography, a peptide prepared by the method and a cosmetic composition and a food composition for preventing or improving skin aging or skin wrinkles including the same.

BACKGROUND

As interest in the elastic and beautiful skin has increased without distinction of sex or age, the cosmetics market is increasingly interested in developing functional substances that can help improve wrinkles for satisfying the desire for beauty instead of conventional health-oriented cosmetics. In particular, the keratin peptide is a natural amino acid polymer (50 or less of amino acid) that forms the basis of the epithelium structure such as hair, nails, and skin and has its excellent interaction with proteins in vivo, thereby having various physiological activities.

In recent years, the cosmetic manufacturing technology has been standardized, and thus the development of novel materials including distinctive natural ingredients has become a vital issue in the cosmetics industry so that a great deal of attention has been paid to the functionality of natural keratin peptides. In Korea, however, functional peptide cosmetics are developed very slowly because of the price burden (about KRW 200 million to 3,000 million per 1 kg) of raw materials for functional peptides being imported, and even if the peptide is included, it is mostly only a tiny amount.

Most of the therapeutic peptides (including vaccines) used for treating human or livestock diseases are expensive products in spite of their tiny amounts. Even if a peptide has a very excellent effect, its size is one of a polymer (molecular weight: 3 kDa or more) composed of 15 amino acids or more. Thus, it is not good for the keratin permeability of the skin and also is not easy to be absorbed into the cell. Therefore, the most critical factors in the new development of peptide materials are 1) peptide efficacy, 2) peptide size (molecular weight), and 3) selective separation and high purity purification technology that determine the unit cost of production.

Currently, it relies on ultrafiltration membranes for the isolation and preparation of low molecular weight peptides industrially used. The expensive pharmaceutical peptides are purified and isolated by complex chromatography methods to be used. In general, reverse phase liquid chromatography (RP-LC) and reverse phase high-performance liquid chromatography (RP-HPLC) using hydrophobic interactions are typical for purifying high molecular substances such as peptides and proteins produced by synthesis or recombinant methods thereof.

RP-LC and RP-HPLC methods are capable of efficiently separating impurities closely related thereto and purifying a large number of various molecules and are particularly being used in mass purification processes for the production of industrial-scale proteins. Particularly, in the reverse phase chromatography, C-4, C-8, and C-18 alkyl chains binding to the surface of silica are used as the medium for purifying peptide proteins. The key to purification in such RP-LC method is the shape and size of the resin particles on the stationary phase, the buffer system, the flow rate, pH thereof, and the like. Despite such technical improvement in the protein purification, some purified proteins still include significant amounts of impurities (for example, having an opposite ion). Particularly, in order to develop functional cosmetic materials, which are not medicines, separation methods using such expensive equipment have very limited economic efficiency and productivity so that it is limited to be applied the practical industries. Therefore, functional ultra-low molecular weight peptides having efficacy shall be efficiently and rapidly obtained, and at the same time, development of an economical and simple chromatographic purification process is highly required to develop new substance of peptide for the natural-derived functional cosmetic.

SUMMARY

Therefore, the present inventors have made an effort to develop a process capable of recovering and separating functional keratin peptides having an anti-aging effect from degradation products of the non-degradable keratin and to develop a purification process that selectively separates ultra-low molecular weight peptides which are capable of efficiently and freely permeating the skin stratum corneum and cell membranes without the aid of delivery systems.

The present disclosure has been made in an effort to provide a method of preparing a keratin peptide for preventing or improving skin aging or skin wrinkles using culturing a microorganism having keratinolytic activity in a medium including keratin, ultrafiltration, ion exchange chromatography, and gel filtration chromatography.

Further, the present disclosure has been made in an effort to provide a keratin peptide mixture prepared by the method and a cosmetic composition and a food composition for preventing or improving skin aging or skin wrinkles including the same.

Further, the present disclosure has been made in an effort to provide a peptide represented by at least one sequence selected from the group consisting of SEQ ID NO: 1 to SEQ ID NO: 9 and a cosmetic composition and a food composition for preventing or improving skin aging or skin wrinkles including the same.

An exemplary embodiment of the present disclosure provides a method of preparing keratin peptide mixture for preventing skin aging and skin wrinkles, the method including the steps of:

(1) obtaining keratin hydrolysates by culturing a microorganism having keratinolytic activity in a culture medium including keratin;

(2) fractionating a protein having a molecular weight of 100 Da to 1000 Da in the keratin hydrolysates obtained from step (1);

(3) purifying the protein by performing ion exchange chromatography, gel filtration chromatography or a combination thereof on the fractionated product obtained from step (2); and (4) purifying and desalting the protein by performing gel filtration chromatography on the purified protein obtained from step (3).

Hereinafter, the present disclosure is described in detail.

The inventor of the present disclosure obtained a large amount of keratin peptides having an anti-skin aging effect by efficiently obtaining keratin degradation products through ultra-high temperature anaerobic fermentation in a minimal restriction medium supplemented with non-degradable poultry feathers as a nutrient source. Further, the hydrolysate of the feather was fractionated by molecular weight using ultrafiltration, thereby recover a large amount of ultra-low molecular weight (1 kDa or less) keratin peptide. Further, the ultra-low molecular weight keratin peptides were separated and purified by ion exchange chromatography and gel filtration chromatography. Furthermore, the purification process is simplified to use only gel filtration chromatography, thereby separating and purifying the ultra-low molecular weight keratin peptides. Further, it was confirmed that these peptides do not exhibit cytotoxicity and have an ability to inhibit MMP-1 activity and ability to inhibit MMP-1 expression. It was confirmed that these peptides have anti-aging function and excellent skin keratin permeability so that they can be used to prevent or improve skin aging and skin wrinkles.

Hereinafter, each step of the present disclosure is described in detail.

Step (1) of the present disclosure is performed to obtain keratin hydrolysates by culturing a microorganism having keratinolytic activity in a culture medium including keratin.

The term 'microorganism having keratinolytic activity' used in the present disclosure includes a microorganism having an activity which is capable of decomposing keratin without limitation and may be preferably a hyperthermophilic microorganism.

The term 'hyperthermophilic microorganism' used in the present disclosure is a kind of extremophile, meaning a microorganism having a relatively high temperature, that is, an optimal growth temperature at about 60° C. or higher, and its kind is not limited. It can be preferably *Fervidobacterium* genus. The *Fervidobacterium* genus may include *islandicum, pennivorans, changbaicum, gondwanense* species. Most preferably, *Fervidobacterium islandicum* AW-1 (KCTC4680) can be used.

The term 'keratin' used in the present disclosure is a kind of structural protein, which is a major component of the cytoskeleton. The keratin is classified into soft keratin and hard keratin depending on cysteine content. The soft keratin includes about 10% to 14% of cysteine and is included in hair, a nail, wool, chicken hair, and the like having many disulfide bonds. In the keratin, structures of α-helix (α-keratin) or β-sheet (β-keratin) are tangled with each other so that protein chains are very tightly packed, and many disulfide bonds, hydrogen bonds and hydrophobic interactions are present in the polypeptide chains so that it is highly stable and highly resistant to proteolytic enzymes.

The keratin of the present disclosure may be derived from a feather, hair, leather, a nail, a claw, a horn or a hoof of a bird or a mammal. Preferably, the feather of the bird may be included in a medium to be used.

The feather of the bird is preferably included in the medium in an amount of 5 g/L to 15 g/L, more preferably 8 g/L. When the content is within the range as described above, the keratin peptide may be prepared through the anaerobic culture within 1 day to 2 days, and it is preferable to obtain appropriate sized functional keratin peptide.

The culture may be a high-temperature culture at 60° C. or higher. The culture temperature is not limited and may be preferably 60° C. to 90° C.

The culture in step (1) may be an anaerobic culture. The method of anaerobic culture is not limited but may be a static anaerobic culture.

In the specific example of the present disclosure, 8 g/L chicken hair is added as a nitrogen source to the growth medium having the composition shown in Table 1, *Fervidobacterium islandicum* AW-1 is anaerobically cultured at 70° C., and the obtained keratin peptide hydrolysates are filtered. Then, the filtered keratin peptide hydrolysates are centrifuged at 10,000×g to precipitate and recover the cells. After filtration, the supernatant is recovered.

The step (2) of the present disclosure is performed to fractionate a protein having a molecular weight of 100 Da to 1000 Da in the keratin hydrolysates obtained from the step (1).

The step (2) may be performed by ultrafiltration, and the pore size of the ultrafiltration membrane used for ultrafiltration in the present disclosure may be 10 kDa to 1 kDa. Preferably, the filtration membrane with 1 kDa may be used finally. Using such a filtration membrane, a keratin peptide fractionated product having a peptide of 1 kDa or less may be obtained.

The step (3) of the present disclosure is performed to purify the protein by performing ion exchange chromatography, gel filtration chromatography or a combination thereof on the fractionated product obtained from the step (2).

The protein is purified by performing ion exchange chromatography, gel filtration chromatography or a combination thereof on the protein product having a size of 1 kDa or less, which is filtered and eluted in step (2).

In the ion exchange chromatography, cross-linked polystyrene or dextran may be used as a resin. The bead size of the resin is not limited but may be 20 μm to 100 μm, preferably 34 μm to 50 μm.

In a specific embodiment of the present disclosure, the ion exchange chromatography includes:

a) filling an ion exchange chromatography column with agarose or dextran-based polymer resin equilibrated with 50 mM Tris-HCl (pH 7.5) of buffer;

b) bringing a keratin peptide sample into the column at a flow rate of about 1 ml or less per minute;

c) washing the column with the same buffer as in the step a); and d) eluting the purified product from the column by performing a linear gradient of sodium chloride having a concentration of 0.1 M to 1 M.

There is no limitation on the type of the buffer, but Tris solvent may be preferably used. Further, the buffer may have a concentration of 20 mM to 50 mM.

In a specific embodiment of the present disclosure, the gel filtration chromatography includes:

a) filling the gel filtration liquid chromatography column with agarose or dextran-based polymer resin equilibrated with sodium chloride having a concentration of 0.1 mol of buffer;

b) bringing the keratin peptide sample into the column at a flow rate of about 0.7 ml or less per minute;

c) washing the column with the same buffer as in the step a); and d) eluting the purified product from the column with the same buffer as in step a).

There is no limitation on the type of the buffer, but Tris solvent may be preferably used. Further, the buffer may have a molar concentration of 20 mM to 50 mM.

The step (4) of the present disclosure is performed to purify and desalt the protein by performing gel filtration chromatography on the purified protein obtained from the step (3).

In a specific embodiment of the present disclosure, the gel filtration chromatography includes:

a) filling the gel filtration liquid chromatography column with agarose or dextran-based polymer resin equilibrated with water of buffer;

b) bringing the keratin peptide sample into the column at a flow rate of about 0.5 ml or less per minute;

c) washing the column with the same buffer as in the step a); and d) eluting the purified product from the column with the same buffer as in step a).

The term 'desalting' used in the present disclosure is a method of removing salts included in a sample. The method is not limited, but ion exchange, size exclusion chromatography, dialysis or gel filtration liquid chromatography may be used. In the present disclosure, a gel filtration liquid chromatography method using water is finally used to completely remove the salts included in the sample.

Further, the present disclosure has been made in an effort to provide a keratin peptide mixture prepared by the method as described above.

In the present disclosure, the keratin peptide mixture is used to include both a set of keratin peptides obtained by the method or at least one keratin peptide which may be identified therefrom.

The keratin peptide prepared in the present disclosure have an inhibitory ability of MMP-1 expression, which is an enzyme causing skin aging, and does not exhibit cytotoxicity so that it is suitable for use as a cosmetic composition, a pharmaceutical composition and a food composition for preventing, improving and treating skin aging and skin wrinkles.

In particular, the keratin peptide of the present disclosure is a keratin peptide having a molecular weight of 100 Da to 1000 Da, which is an ultra-low molecular peptide and thus has excellent stratum corneum permeability.

Further, the present disclosure has been made in an effort to provide a cosmetic composition for preventing or improving skin aging or skin wrinkles, the composition including the keratin peptide mixture.

The keratin peptide of the present disclosure has an inhibitory ability of MMP-1 expression, thereby exhibiting an effect of preventing skin aging or skin wrinkles.

The keratin peptide of the present disclosure has an ability to inhibit MMP-1 activity, thereby exhibiting an effect of preventing skin aging or skin wrinkles.

The keratin peptide of the present disclosure has an effect of preventing skin aging or skin wrinkles caused by ultraviolet rays.

The keratin peptide of the present disclosure is preferably included in an amount of 0.001% to 50% by weight with respect to the total weight of the cosmetic composition but is not limited thereto.

The cosmetic composition of the present disclosure may further include conventional carriers and auxiliary agents such as antioxidants, stabilizers, solubilizers, vitamins, pigments, perfumes which are conventionally used in cosmetic compositions in addition to the active ingredients. For example, the cosmetic composition may further include an auxiliary component such as glycerin, butylene glycol, polyoxyethylene hardened castor oil, tocopheryl acetate, citric acid, panthenol, squalane, sodium citrate, and allantoin.

Since the cosmetic composition of the present disclosure is basically applied to the skin, it may be prepared in any formulation conventionally prepared by referring to the cosmetic composition of the related art. For example, it may, but is not limited to, be formulated as a solution, a suspension, an emulsion, a paste, a gel, cream, a lotion, a powder, a soap, surfactant-including cleansing, an oil, powder foundation, emulsion foundation, wax foundation, a spray, and the like. More specifically, it may be prepared in the form of a soft lotion, a nutritional lotion, nutritional cream, massage cream, an essence, eye cream, cleansing cream, cleansing foam, cleansing water, a mask pack, a spray or a powder.

When the formulation of the present disclosure is a paste, cream or a gel, the carrier component includes an animal oil, a vegetable oil, wax, paraffin, starch, tracant, a cellulose derivative, polyethylene glycol, silicon, bentonite, silica, talc, zinc oxide, and the like.

When the formulation of the present disclosure is a powder or a spray, the carrier component may include lactose, talc, silica, aluminum hydroxide, calcium silicate, polyamide powder, and the like. In particular, when the formulation is a spray, the carrier component may further include a propellant such as chlorofluorohydrocarbons, propane/butane, and dimethyl ether.

When the formulation of the present disclosure is a solution or an emulsion, the carrier component may include a solvent, a solubilizer, an emulsifier, and the like. Specific examples thereof include water, ethanol, isopropanol, ethyl carbonate, ethyl acetate, benzyl alcohol, benzyl benzoate, propylene glycol, 1,3-butylglycol oil, glycerol aliphatic ester, polyethylene glycol, fatty acid esters of sorbitan, and the like.

When the formulation of the present disclosure is a suspension, the carrier component may include a liquid diluent such as water, ethanol and propylene glycol; a suspending agent such as ethoxylated isostearyl alcohol, polyoxyethylene sorbitol ester and polyoxyethylene sorbitan ester; microcrystalline cellulose, aluminum metahydroxide, bentonite, agar, tracant, and the like.

When the formulation of the present disclosure is a surfactant-including cleansing, the carrier component may include an aliphatic alcohol sulfate, aliphatic alcohol ether sulfate, sulfosuccinic acid monoester, isethionate, imidazolinium derivative, methyltaurate, sarcosinate, fatty acid amide ether sulfate, alkylamidobetaine, aliphatic alcohol, fatty acid glyceride, fatty acid diethanolamide, a vegetable oil, a lanolin derivative, ethoxylated glycerol fatty acid ester, and the like.

Further, the present disclosure has been made in an effort to provide a food composition for preventing or improving anti-aging or anti-wrinkles, in which the composition includes the keratin peptide compound.

When the keratin peptide of the present disclosure is used as a food additive, the keratin peptide may be used as it is or may be used suitably depending on a conventional method such as mixing with another food or food ingredient.

Further, the mixing amount of the keratin peptide as an active ingredient may suitably change depending on the intended use (prevention, health or therapeutic treatment), and the keratin peptide is included in an amount of 0.001% by weight to 50% by weight with respect to the total weight of the food composition but is not limited thereto.

As a specific example, when preparing a food or a beverage, the keratin peptide of the present disclosure is added in an amount of 15% by weight or less, preferably 10% by weight or less, with respect to the raw material. However, in case of health and hygiene purposes or long-term intake for the purpose of controlling health, it may be added in an amount of the range or less, and since there is no issue in safety, the active ingredient may be used in an amount of the range or more.

There is no particular limitation on the kind of the food. Examples of foods to which the keratin peptide of the present disclosure is added include meat, sausage, bread, chocolate, candy, snack, confectionery, pizza, ramen, other noodles, gum, a dairy product including ice cream, various soups, beverage, tea, drink, an alcoholic beverage, a vitamin complex, and the like and include all health foods in the usual meaning.

When the food composition of the present disclosure is prepared as a beverage, it may include an additional ingredient such as various flavors or natural carbohydrates like conventional beverages. Examples of the natural carbohydrate include a monosaccharide such as glucose and fructose; a disaccharide such as maltose and sucrose; a natural sweetener such as dextrin and cyclodextrin and a synthetic sweetener such as saccharin and aspartame. The natural carbohydrate is included in an amount of 0.01% by weight to 10% by weight, preferably 0.01% by weight to 0.1% by weight with respect to the total weight of the food composition of the present disclosure.

In addition to the above description, the food composition of the present disclosure includes various nutrients, a vitamin, an electrolyte, a flavor, a colorant, pectic acid and its salt, alginic acid and its salt, organic acid, a protective colloid thickener, a pH adjuster, a stabilizer, a preservative, glycerin, an alcohol, a carbonating agent used in a carbonated drink, and the like. In addition, the composition of the present disclosure may include a natural fruit juice, flesh for the production of a fruit juice beverage and a vegetable beverage. These components may be used independently or in combination. The proportion of the additive is not particularly limited but is preferably within the range of 0.01% by weight to 0.1% by weight with respect to the total weight of the food composition of the present disclosure.

Further, the present disclosure has been made in an effort to provide a pharmaceutical composition for preventing or treating skin aging or skin wrinkles, in which the composition includes the keratin peptide mixture as an active ingredient.

The content of the keratin peptide included in the pharmaceutical composition for preventing or treating skin aging or skin wrinkles of the present disclosure may be appropriately adjusted depending on the method of using the therapeutic agent, the condition of the recipient, the type of disease and the severity thereof. In the pharmaceutical composition of the present disclosure, the keratin peptide is preferably included in an amount of 0.001% by weight to 50% by weight but is not limited thereto.

The composition of the present disclosure may further include a suitable carrier, an excipient and a diluent conventionally used in the preparation of the pharmaceutical composition. Further, it may be formulated in the form of an oral formulation such as a powder, a granule, a tablet, a capsule, a suspension, an emulsion, syrup and an aerosol, an external preparation, a suppository and a sterilized injection solution according to a conventional method. Suitable formulations known in the art are preferably those disclosed in documents (Remington's Pharmaceutical Science recent edition (Mack Publishing Company, Easton Pa.)). Examples of a carrier, an excipient and a diluent that may be included include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinyl pyrrolidone, water, methylhydroxybenzoate, propylhydroxy benzoate, talc, magnesium stearate, mineral oil, and the like. When the composition is formulated, it is prepared using a diluent or an excipient such as a filler, an extender, a binder, a wetting agent, a disintegrant or a surfactant usually used. The solid preparation for oral administration includes a tablet, a pill, a powder, a granule, a capsule, and the like and is prepared by mixing at least one excipient such as starch, calcium carbonate, sucrose, lactose, gelatin to the composition. A lubricant such as magnesium stearate and talc is also used in addition to a simple excipient. The liquid preparation for oral administration includes a suspension, a solution, an emulsion, syrup, and the like. Various excipients such as a wetting agent, a sweetener, a fragrance, and a preservative may be included in addition to commonly used simple diluents such as water and liquid paraffin. Formulation for parenteral administration includes a sterilized aqueous solution, a non-aqueous solution, a suspension, an emulsion, a freeze-dried preparation, a suppository, and the like. Examples of the non-aqueous solution and the suspension include propylene glycol, polyethylene glycol, an vegetable oil such as an olive oil, an injectable ester such as ethyl oleate. Witepsol, macrogol, tween 61, cacao paper, laurin, glycerogelatin and the like may be used as the base of suppositories.

The term 'administration' used in the present disclosure refers to providing the given composition of the present disclosure to an object in any suitable scheme.

The pharmaceutical composition of the present disclosure may be administrated in an amount of a pharmaceutical composition or an active ingredient that induces a biological or medical response in a tissue system, animal or human, as contemplated by a researcher, a veterinarian, a physician or other clinicians, that is, a therapeutically effective amount, which is an amount that induces the relief of the symptoms of the disease or disorder being treated. It will be apparent to those skilled in the art that the therapeutically effective amount and frequency of administration of the pharmaceutical composition of the present disclosure vary depending on the desired effect. Thus, the optimal amount to be administered may be readily determined by those skilled in the art and may be readily adjusted depending on various factors such as the kind of the disease, the severity of the disease, the amount of active and other ingredients included in the composition, the type of formulation, age, body weight, normal health condition, sex, and diet of the patient, the time of administration, the route of administration, the secretion rate of the composition, the duration of the treatment, and the drugs used concurrently. For the desired effect, the pharmaceutical composition of the present disclosure may be administered in an amount of 1 mg/kg/day to 10,000 mg/kg/day, preferably 1 mg/kg/day to 200 mg/kg/day. It may be administered once a day or to be divided into several doses.

The pharmaceutical composition of the present disclosure may be administered to an object in a variety of routes. All schemes of administration may be expected, for example, it can be administrated by oral, rectal, intravenous, intramuscular, subcutaneous, intra-uterine dural or intracerebral injection.

Further, the present disclosure has been made in an effort to provide a peptide represented by at least one sequence selected from the group consisting of SEQ ID NO: 1 to SEQ ID NO: 9.

The peptide represented by SEQ ID NO: 1 to SEQ ID NO: 9 is prepared by the method of preparing the keratin peptide of the present disclosure, which is amino acid sequence synthesized and identified by LC-MS/MS for the keratin peptide having the anti-aging ability. More specifically, the peptide may be obtained using a database constructed based on a keratin sequence of a target substance and a cleavage site of a keratin-degrading protease and peptide of a strain, for example, AW-1 strain, which is capable of degrading the keratin. It may be synthesized using conventional techniques in the art based on sequences obtained by performing LC/MS-MS in the database to identify the peptide. The peptide has an ultra-low molecular weight of 1 kDa or less and exhibits an effect of inhibiting MMP-1 expression induced by ultraviolet B and an effect of inhibiting MMP-1 activity so that it can be usefully used for preventing or improving skin aging or skin wrinkles.

Further, the present disclosure has been made in an effort to provide a cosmetic composition for preventing or improving skin aging or skin wrinkles, including a peptide represented by at least one sequence selected from the group consisting of SEQ ID NO: 1 to SEQ ID NO: 9.

Further, the present disclosure has been made in an effort to provide a food composition for preventing or improving skin aging or skin wrinkles, including a peptide represented by at least one sequence selected from the group consisting of SEQ ID NO: 1 to SEQ ID NO: 9.

According to the exemplary embodiments of the present disclosure, it is possible to eco-friendly biologically treat waste resources and efficiently purify and recover anti-aging functional ultra-low molecular weight keratin peptides. In addition, the keratin peptide of the present disclosure have an ability to inhibit MMP-1 expression and ability to inhibit MMP-1 activity, which is an enzyme that causes skin aging, which has an excellent effect on anti-skin aging and skin wrinkle improvement and has no toxicity to skin cells. It is suitable for use as a cosmetic composition, a pharmaceutical composition or a food composition for preventing, improving or treating skin aging or skin wrinkles, thereby being efficiently used for the efficient and rapid production and development of high value-added functional cosmetic substances.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 1 is a schematic view of a method of preparing keratin peptides,

FIG. 2 illustrates the results of fractionation of keratin peptides having 1 kDa or less by ion exchange chromatography and gel filtration chromatography, FIG. 3 illustrates the results of fractionation of keratin peptides having 1 kDa or less using gel filtration chromatography, FIG. 4A and FIG. 4B illustrate the results (FIG. 4A) of the toxicity test of ultra-low molecular weight peptide of the present disclosure in human dermal fibroblasts and the results (FIG. 4B) measuring an effect of inhibiting MMP-1 expression induced by ultraviolet B (UVB), in which lane 1 was a non-treated control group, lane 2 was a group treated with 20 mJ/cm$^2$ UVB alone, and lanes 3, 4, 5, 6, 7 and 8 were experimental groups treated with 20 mJ/cm$^2$ ultraviolet B (UVB) and keratin peptide mixtures (No. 2 and KP 7) at 5, 10 and 20 μg/mL of the present disclosure, and FIGS. 5A-5C illustrate the results (FIG. 5A) of the test on inhibiting MMP-1 activity by the synthetic keratin peptide of Table 3, the results (FIG. 5B) of the toxicity test of human dermal fibroblasts and the results (FIG. 5C) measuring an effect of inhibiting MMP-1 expression induced by ultraviolet B (UVB), in which lane 1 was a non-treated control group, lane 2 was a group treated with 20 mJ/cm$^2$ UVB alone, and lanes 3 and 4 were experimental groups treated with 20 mJ/cm$^2$ ultraviolet B (UVB) and synthetic keratin peptide mixtures with 10 μM.

DETAILED DESCRIPTION

In the following detailed description, reference is made to the accompanying drawing, which forms a part hereof. The illustrative embodiments described in the detailed description, drawing, and claims are not meant to be limiting. Other embodiments may be utilized, and other changes may be made, without departing from the spirit or scope of the subject matter presented here.

Hereinafter, the present disclosure is described in more detail with reference to examples. However, these examples are provided to illustrate the present disclosure, and the scope of the present disclosure is not limited to these examples.

Example 1. Preparation of Keratin Peptide 1.1 Culture and Preparation of Keratin Hydrolysate For the preparation of a keratin peptide mixture, *Fervidobacterium islandicum* AW-1 (KCTC4680), a chicken hair degrading strain, was anaerobically cultured as a nitrogen source in a growth medium supplemented with chicken hair at 70° C. as shown in Table 1 below to obtain keratin hydrolysate.

TABLE 1

| Culture components | Amount (g/L) |
| --- | --- |
| NH$_4$Cl | 0.1 |
| NaH$_2$PO$_4$•2H$_2$O | 0.9 |
| MgSO$_4$•7H$_2$O | 0.16 |
| K$_2$HPO$_4$ | 1.6 |
| Vitamin solution (DSM 141) | 10 ml |
| Trace element solution (DSM 141) | 10 ml |
| 0.1% Resazurin | 1 ml |
| Yeast extract | 1.0 |
| Chicken hair | 8.0 |
| Na$_2$S (25%, w/v) | 3 ml |

Then, the keratin hydrolysate was first filtered using a filter paper (5 μm, No. 20, Hyundai Micro, Korea) to produce the degraded chicken hair remnant and centrifuged at 10,000×g for 20 minutes at 4° C. to recover supernatant. The recovered supernatant was used as a sample for the separation and purification of functional ultra-low molecular weight keratin peptides.

1.2 Purification of Keratin Hydrolysate

Ultrafiltration was used to easily fractionate ultra-low molecular weight keratin peptides having a size of 1 kDa or less from the sample. In the ultrafiltration, membranes with pore size of 10 kDa and 1 kDa were used as ultrafiltration membranes. Specifically, the sample was introduced into a filtration module equipped with a filtration membrane, and a pressure of about 10 to 30 psi was applied to allow the sample to pass through the filtration membrane so that it was filtered. First, proteins having a size of 10 kDa or more was isolated using a 10 kDa ultrafiltration membrane, and proteins having a size of 10 kDa or less flowed out from the filtration module was fractionated into a sample having a size of 1 kDa or more and a sample having a size of 1 kDa or less using an 1 kDa ultrafiltration membrane.

For the fractionated keratin peptide sample having a size of 1 kDa or less, keratin peptides were purified by two methods: i) purification by ion exchange chromatography. The fractionated sample was separated and purified depending on an ionic character by ion exchange chromatography using a Biologic duo-flow FPLC system (Bio-rad) and Macro-prep DEAE support (Bio-Rad) (50 mM Tris-HCl buffer, pH 7.5, 0 M-1 M NaCl). The results are illustrated in FIG. 2. As illustrated in FIG. 2, two peaks were observed at 210 nm, and the relative cationic Fr. 4-47 were pooled and lyophilized. For desalt and separation based on the molecular weight, the lyophilized sample was subjected to gel filtration chromatography (20 mM Tris-HCl buffer, pH 7.0, 100 mM NaCl) using Bio-rad biologic duo-flow FPLC system and superdex 30 pg (GE). Four peaks were observed at 210 nm. Fr. 16-29, expected to include a keratin peptide compared to the reference material, were pooled and lyophilized. Hereinafter, the keratin peptide obtained by the above method is referred to as No. 2;

ii) purification by gel filtration chromatography. The fractionated sample was subjected to gel filtration chromatography in the same manner as described in i). The results are illustrated in FIG. 3. As illustrated in FIG. 3. Fr. 17-26 were pooled and lyophilized. Hereinafter, the keratin peptide obtained by the above method is referred to as KP7.

The absorbance of the samples was measured at 280 nm and 210 nm in order to measure the amounts of protein and peptide upon performing chromatography.

To confirm the desalting and molecular weight of the finally separated and purified No. 2 and KP7 samples, gel filtration chromatography was performed using Superdex peptide 10/300 GL (GE). It was confirmed to be an ultra-low molecular weight keratin peptide having a molecular weight of 1 kDa or less (See FIGS. 2 and 3). Further, they were used in the following examples.

Example 2. Cytotoxicity Test of Keratin Peptide in Human Dermal Fibroblasts and Effect of Inhibiting MMP-1 Expression Induced by UVB MTT assay was performed using human dermal fibroblasts to examine the cytotoxicity of the keratin peptide prepared by the method of Example 1 as described above.

First, human fibroblasts were divided into 96-well plates in a density of $5 \times 10^3$ cells/well, and each of them was cultured using a medium supplemented with Dulbecco's Modified Eagle's Medium (DMEM) including 10% fetal bovine serum (FBS) and penicillin-streptomycin (GIBCO Invitrogen, Auckland, NZ) under a condition of 37° C. and 5% $CO_2$ for 6 hours. 200 mg of MTT (3-(4,5-dimethylthiazol-2-yl)-2,5-diphenyl-tetrazolium bromide) powder was dissolved in 40 mL of PBS and filtered to prepare 5 mg/mL MTT solution. After 6 hours therefrom, the medium including the prepared keratin peptide was added, and after 72 hours, 20 μL of 5 mg/ml MTT solution was added. After culture for 3 hours, medium and MTT solution were removed, and 200 μL of dimethyl sulfoxide (DMSO) was added and mixed at room temperature for 30 minutes. The absorbance of the reaction mixture was measured at 570 nm using a microplate reader (Sunrise-Basic Tecan, Austria), and the cell survival rate thereof was calculated according to the following Equation 1. The result of calculation of cell survival rate is illustrated in FIG. 4A.

Cell survival rate(%)=100−((absorbance of non-treated control group−absorbance of sample-added group)/absorbance of non-treated control group×100)     [Equation 1]

As illustrated in FIG. 4A, the keratin peptide of the present disclosure exhibited no cytotoxicity up to a concentration of 100 μg/mL.

In order to measure the expression level of MMP-1 in the cells, the keratin peptides of the present disclosure were dissolved in sterilized water at a concentration of 5, 10, and 20 μg/mL in human-derived human dermal fibroblast. Then, ultraviolet ray B was irradiated with 20 mJ/cm$^2$ using Vilber Lourmat (BioLink Crosslinker, France), cultured for 24 hours, and then cell proteins were recovered. At this time, the medium was removed before ultraviolet irradiation, and then washed with phosphate buffered saline (PBS) solution to remove serum components in the medium and then irradiated with ultraviolet ray B. The cells were washed twice with PBS solution to recover the proteins, and then the cells adhered to the bottom were recovered using a lysis buffer and centrifuged at 14,000 rpm for 10 minutes. After each supernatant was recovered, the protein concentration of each cell supernatant was quantified according to the method of use with a protein assay kit (Bio-Rad, USA) using bovine serum albumin (BSA) as the reference material. About 10 mg protein from each of the protein extracts was denatured and separated by 8% gel sodium dodecyl sulphate-polyacrylamide gel electrophoresis (SDS-PAGE) and transferred to a polyvinylidene fluoride (PVDF) membrane at 120 mA for 2 hours. Then, the cells were immersed in a TBS-T solution including 5% skim milk for 6 hours to block non-specific proteins, washed once with distilled water and twice with TBS-T. At this time, Matrix Metalloprotease-1 (MMP-1) monoclonal antibody (Neo Markers, Fremont, Calif.) was diluted with a TBS-T solution at a ratio of 1:1,000 to be used and reacted at 4° C. overnight. After the primary antibody reaction, the cells were washed twice with TBS-T for 15 minutes. Horseradishperoxidase (HRP)-bound anti-rabbit IgG (Santacruz, USA) was diluted at a ratio of 1:5,000 to be used as the secondary antibody and reacted at a room temperate for 1 hour and 30 minutes. After the reaction, the cells were washed with TBS-T 4 times for 5 minutes and reacted with ECL substrate (Amersham TM, UK) for 5 minutes. Then, the cells were sensitized to X-ray film to analyze changes in expression of the cell aging-related protein. The results of the above experiment are illustrated in FIG. 4B.

As illustrated in FIG. 4B, when No. 2 was treated at a concentration of 10 μg/mL or more and KP7 was treated at a concentration of 5 μg/mL or more, it was confirmed that the expression of MMP-1 was significantly inhibited compared to the only UVB-treated group.

Therefore, the keratin peptide of the present disclosure has no toxicity to skin cells and has an excellent effect of inhibiting MMP-1 expression even under a condition of ultraviolet irradiation so that it can be used as a cosmetic or food composition for preventing, improving and treating skin aging and skin wrinkles. In particular, it was confirmed that the keratin peptide could be used for improving skin aging and skin wrinkles caused by UVB.

In addition, in the prior patent (Patent Application No. 10-2014-0092000), it was confirmed that the groups treated keratin peptide of 1 kDa or less at a concentration of 200 μg/ml and 400 μg/ml, respectively, exhibited about 12% and 41% of an effect of inhibiting MMP-1 expression compared to only UVB-treated group, but No. 2 and KP7 inhibited the expression of MMP-1 at a lower concentration as compared with the former. This indicates that the keratin peptide prepared by the method of purifying ultra-low molecular weight keratin peptide using Example 1 of the present disclosure has a high effect of preventing, improving and treating skin aging and skin wrinkles.

Example 3. Identification and Synthesis of Amino Acid Sequence of Keratin Peptide The peptides were identified using LC-MS/MS in order to confirm amino acid sequences of the keratin peptides having such activity in No. 2 and KP 7 in which the anti-aging ability and the wrinkle improving ability were confirmed as described above.

Specifically, a feather keratin sequence of chicken (*Gallus gallus* ver. 5.0) was obtained from Genbank to construct a database for keratin peptide mapping. By transcript analysis of AW-1 strain, selection of proteases involved in degrading the chicken hair and peptide cleavage sites were confirmed, and a database was constructed for analysis of LC-MS/MS results based thereon. As the mass spectrometer, ESI-Q-TOF (Thermo (Dionex) UHPLC Ultimate 3000, ABsciex Triple TOF 5600+) was used. The keratin peptides whose separation, purification and anti-aging ability were evaluated by the method were identified to reveal 16 kinds derived from No. 2 and 8 kinds derived from KP7, which were ultra-low molecular weight peptide having a molecular weight of 1 kDa or less (at least 445.3 Da to at most 710.3 Da). Those are shown in Table 2 below.

TABLE 2

| No. | Sample | Sequence | Theoretical molecular weight |
|---|---|---|---|
| 1 | No. 2, KP7 | GGFGL | 449.2 |
| 2 | No. 2 | GGFGI | 449.2 |
| 3 | No. 2 | FGGFG | 483.2 |
| 4 | No. 2 | GFGGF | 483.2 |
| 5 | No. 2 | GPTPL | 483.3 |
| 6 | No. 2 | GLGSR | 488.3 |
| 7 | No. 2 | PISGGF | 576.3 |
| 8 | No. 2 | SFPQN | 591.3 |
| 9 | No. 2 | GGFGGFG | 597.3 |
| 10 | No. 2 | FPQNT | 605.3 |
| 11 | No. 2 | SSGGFGI | 623.3 |
| 12 | No. 2 | SSGGFGL | 623.3 |
| 13 | No. 2 | SGGFGGF | 627.3 |
| 14 | No. 2 | GFGGFGL | 653.3 |
| 15 | No. 2 | PISSGGF | 663.3 |
| 16 | No. 2 | GGFGGFGL | 710.3 |
| 17 | KP7 | GLSGL | 445.3 |
| 18 | KP7 | SGGFGI | 536.3 |
| 19 | KP7 | GGFGGF | 540.2 |
| 20 | KP7 | GVPISS | 558.3 |
| 21 | KP7 | SGGFGF | 570.2 |
| 22 | KP7 | IQPSPV | 639.4 |
| 23 | KP7 | GVPISSGG | 672.3 |
| 24 | KP7 | SFPQNT | 692.3 |

Further, for confirming sequences of peptides having anti-aging ability, 9 kinds of peptides were synthesized based on the results of identifying peptides as shown in Table 3 below.

TABLE 3

| No. | Name | Sequence |
|---|---|---|
| 1 | 2n7-1 | SGGFG |
| 2 | 2n7-2 | PISS |
| 3 | 2n7-3 | GGFGGFGI |
| 4 | 2n7-4 | GFGGF |
| 5 | 2n7-5 | FPQN |
| 6 | KP7-1 | GLSGL |
| 7 | KP7-2 | IQPSPV |
| 8 | 2-1 | GPTPL |
| 9 | 2-2 | GLGSR |

Example 4. Evaluation of MMP-1 Enzyme Activity Inhibition in In Vitro Assay of Synthetic Peptide MMP-1 Fluorometric Drug Discovery Kit manufactured by Enzo company was used to evaluate an ability to inhibit Matrix metalloproteinase-1 (MMP-1) enzyme activity in the peptide synthesized in Example 3. N-Isobutyl-N-(4-methoxyphenylsulfonyl) glycyl hydroxamic acid (NNGH) which is known to inhibit MMP-1 activity was used as a positive control group, and NNGH was treated at a concentration of 0.65 μM. As a sample-added group, a mixture solution in which MMP-1 enzyme and keratin peptides were mixed at 1, 5 and 10 μg/mL was reacted at 37° C. for 5 minutes. The substrate was added to the reaction mixture, fluorescence thereof was measured at Ex/Em=540/590 nm, and the ability to inhibit MMP-1 activity was evaluated according to the following Equation 2. The results of the ability of inhibiting MMP-1 activity are illustrated in FIG. 5A.

$$\text{Ability to inhibit MMP-1activity(\%)} = \text{Fluorescence intensity of sample-added group/Fluorescence intensity of non-treated group} \times 100 \quad \text{[Equation 2]}$$

As illustrated in FIG. 5A, it was confirmed that the synthetic peptides inhibited the activity of MMP-1 enzyme compared to the group treated with the only MMP-1 enzyme at concentrations of 10 μM in 2n7-2, 2n7-4, 2n7-5, KP7-1, KP7-2, 2-1 and 2-2. In particular, it was confirmed that peptide 2n7-4, KP7-1, KP7-2, 2-1 and 2-2 had a significant effect of inhibiting MMP-1 activity.

Example 5. Cytotoxicity Test in Human Fibroblasts and Inhibitory Effect of MMP-1 Expression Induced by Ultraviolet B In order to examine the cytotoxicity of the peptides synthesized in Example 3, MTT assay using human dermal fibroblast was performed in the same manner as in Example 2. The results of the experiment are illustrated in FIG. 5B.

As illustrated in FIG. 5B, the synthetic peptide of the present disclosure did not exhibit cytotoxicity up to a concentration of 100 μg/mL.

In order to measure the expression of MMP-1 in cells, synthetic peptides 2-1 and 2-2 were dissolved in DMSO and treated at a concentration of 10 μM in the cultured human dermal fibroblasts derived from human. The method was carried out in the same manner as in Example 2 as described above. The results of measurement of MMP-1 expression are illustrated in FIG. 5C.

As illustrated in FIG. 5C, it was confirmed that when synthetic peptides 2-1 and 2-2 were treated at a concentration of 10 μM, the expression of MMP-1 was inhibited by about 24% and 35%, respectively, compared to the group treated with the only UVB.

From the foregoing, it will be appreciated that various embodiments of the present disclosure have been described herein for purposes of illustration and that various modifications may be made without departing from the scope and spirit of the present disclosure. Accordingly, the various embodiments disclosed herein are not intended to be limiting, with the true scope and spirit being indicated by the following claims.

What is claimed is:

1. A method for preventing or improving skin aging or skin wrinkles, the method comprising the step of treating a skin of subject with a cosmetic composition comprising a peptide comprising at least one sequence selected from the group consisting of SEQ ID NO: 1 to SEQ ID NO: 9.

2. The method of claim 1, wherein the peptide is prepared by a method comprising the steps of:
    (1) obtaining keratin hydrolysates by culturing a microorganism having keratinolytic activity in a culture medium including keratin;
    (2) fractionating a protein having a molecular weight of 100 Da to 1000 Da in the keratin hydrolysates obtained from step (1);
    (3) purifying the protein by performing ion exchange chromatography, gel filtration chromatography or a combination thereof on the fractionated product obtained from step (2); and
    (4) purifying and desalting the protein by performing gel filtration chromatography on the purified protein obtained from step (3).

3. The method of claim 2, wherein the microorganism in step (1) is *Fervidobacterium islandicum* AW-1 (KCTC4680).

4. The method of claim 2, wherein the keratin in step (1) is derived from a feather, hair, leather, a nail, a claw, a horn or a hoof of a bird or a mammal.

5. The method of claim 2, wherein the keratin in step (1) is derived from a feather of a bird.

6. The method of claim 5, wherein the feather is present in the culture medium in an amount of 5 g/L to 15 g/L.

7. The method of claim 2, wherein the culture in step (1) is an anaerobic culture.

8. The method of claim 2, wherein the culture in step (1) is a static anaerobic culture.

9. The method of claim 2, wherein the keratin peptide has an ability to inhibit matrix metalloproteinase-1 (MMP-1) expression or ability to inhibit MMP-1 activity.

10. The method of claim 2, wherein the culture in step (1) is an anaerobic culture performed under a temperature condition of 60° C. to 90° C.

11. The method of claim 2, wherein the fraction in step (2) is performed by ultrafiltration.

12. The method of claim 1, wherein the skin aging is caused by ultraviolet rays.

13. The method of claim 1, wherein the skin wrinkles is caused by ultraviolet rays.

14. The method of claim 1, wherein the cosmetic composition comprising a peptide comprises SEQ ID NO: 9.

15. The method of claim 1, wherein the cosmetic composition comprises a first peptide comprising SEQ ID NO: 9 and a second peptide selected from the group consisting of SEQ ID NO: 1 to SEQ ID NO: 8.

* * * * *

SEQUENCE LISTING

```
<160> NUMBER OF SEQ ID NOS: 9

<210> SEQ ID NO 1
<211> LENGTH: 5
<212> TYPE: PRT
<213> ORGANISM: Artificial Sequence
<220> FEATURE:
<223> OTHER INFORMATION: keratin peptide

<400> SEQUENCE: 1

Ser Gly Gly Phe Gly
1               5

<210> SEQ ID NO 2
<211> LENGTH: 4
<212> TYPE: PRT
<213> ORGANISM: Artificial Sequence
<220> FEATURE:
<223> OTHER INFORMATION: keratin peptide

<400> SEQUENCE: 2

Pro Ile Ser Ser
1

<210> SEQ ID NO 3
<211> LENGTH: 8
<212> TYPE: PRT
<213> ORGANISM: Artificial Sequence
<220> FEATURE:
<223> OTHER INFORMATION: keratin peptide

<400> SEQUENCE: 3

Gly Gly Phe Gly Gly Phe Gly Ile
1               5

<210> SEQ ID NO 4
<211> LENGTH: 5
<212> TYPE: PRT
<213> ORGANISM: Artificial Sequence
<220> FEATURE:
<223> OTHER INFORMATION: keratin peptide

<400> SEQUENCE: 4

Gly Phe Gly Gly Phe
1               5

<210> SEQ ID NO 5
<211> LENGTH: 4
<212> TYPE: PRT
<213> ORGANISM: Artificial Sequence
<220> FEATURE:
<223> OTHER INFORMATION: keratin peptide

<400> SEQUENCE: 5

Phe Pro Gln Asn
1

<210> SEQ ID NO 6
<211> LENGTH: 5
```

```
<212> TYPE: PRT
<213> ORGANISM: Artificial Sequence
<220> FEATURE:
<223> OTHER INFORMATION: keratin peptide

<400> SEQUENCE: 6

Gly Leu Ser Gly Leu
1               5

<210> SEQ ID NO 7
<211> LENGTH: 6
<212> TYPE: PRT
<213> ORGANISM: Artificial Sequence
<220> FEATURE:
<223> OTHER INFORMATION: keratin peptide

<400> SEQUENCE: 7

Ile Gln Pro Ser Pro Val
1               5

<210> SEQ ID NO 8
<211> LENGTH: 5
<212> TYPE: PRT
<213> ORGANISM: Artificial Sequence
<220> FEATURE:
<223> OTHER INFORMATION: keratin peptide

<400> SEQUENCE: 8

Gly Pro Thr Pro Leu
1               5

<210> SEQ ID NO 9
<211> LENGTH: 5
<212> TYPE: PRT
<213> ORGANISM: Artificial Sequence
<220> FEATURE:
<223> OTHER INFORMATION: keratin peptide

<400> SEQUENCE: 9

Gly Leu Gly Ser Arg
1               5
```